(12) United States Patent
Rose et al.

(10) Patent No.: US 7,524,891 B2
(45) Date of Patent: Apr. 28, 2009

(54) BIODEGRADABLE POLYMER SYSTEMS

(75) Inventors: John Rose, York (GB); Steven Hardwick, York (GB)

(73) Assignee: Smith & Nephew PLC (GB)

( * ) Notice: Subject to any disclaimer, the term of this patent is extended or adjusted under 35 U.S.C. 154(b) by 542 days.

(21) Appl. No.: 10/482,371

(22) PCT Filed: Jul. 3, 2002

(86) PCT No.: PCT/GB02/03072

§ 371 (c)(1),
(2), (4) Date: Jun. 29, 2004

(87) PCT Pub. No.: WO2003/004071

PCT Pub. Date: Jan. 16, 2007

(65) Prior Publication Data

US 2004/0242722 A1    Dec. 2, 2004

(30) Foreign Application Priority Data

Jul. 4, 2001    (GB) ................................. 0116341.9

(51) Int. Cl.
*C08K 5/092* (2006.01)
*A61F 2/02* (2006.01)
(52) U.S. Cl. ........................ 523/124; 523/113; 524/284; 524/600
(58) Field of Classification Search ................. 524/284, 524/600; 523/113, 124
See application file for complete search history.

(56) References Cited

U.S. PATENT DOCUMENTS

| | | | |
|---|---|---|---|
| 3,531,561 A | 9/1970 | Trebu | |
| 3,636,956 A | 1/1972 | Schneider | |
| 3,736,646 A | 6/1973 | Schmitt | |
| 3,797,499 A | 3/1974 | Schneider | |
| 4,137,921 A | 2/1979 | Okuzumi | |
| 4,181,983 A | 1/1980 | Kulkarni | |
| 4,438,253 A | 3/1984 | Casey et al. | |
| 4,523,591 A | 6/1985 | Kaplan | |
| 4,539,981 A | 9/1985 | Tung | |
| 4,559,945 A | 12/1985 | Koelmel et al. | |
| 4,636,215 A | 1/1987 | Schwartz | |
| 4,700,704 A | 10/1987 | Jamiolkowski et al. | |
| 4,776,329 A | 10/1988 | Treharne | |
| 4,840,632 A | 6/1989 | Kampner | |
| 4,858,603 A | 8/1989 | Clemow et al. | |
| 4,938,763 A | 7/1990 | Dunn et al. | |
| 4,950,258 A | 8/1990 | Kawai et al. | |
| 4,968,317 A | 11/1990 | Tormala et al. | |
| 4,990,161 A | 2/1991 | Kampner | |
| 5,049,591 A | 9/1991 | Hayashi et al. | |
| 5,108,755 A | 4/1992 | Daniels et al. | |
| 5,110,852 A | 5/1992 | Gogolewski et al. | |
| 5,192,301 A | 3/1993 | Kamiya | |
| 5,201,738 A | 4/1993 | Scott et al. | |
| 5,201,771 A | 4/1993 | Belykh et al. | |
| 5,266,608 A | 11/1993 | Katz et al. | |
| 5,275,601 A | 1/1994 | Gogolewski et al. | |
| 5,294,395 A | 3/1994 | Broyer | |
| 5,333,624 A | 8/1994 | Tovey | |
| 5,360,448 A | 11/1994 | Thramann | |
| 5,364,400 A | 11/1994 | Rego, Jr. et al. | |
| 5,376,120 A | 12/1994 | Sarver et al. | |
| 5,383,931 A | 1/1995 | Hehli et al. | |
| 5,407,445 A | 4/1995 | Tautvydas et al. | |
| 5,417,712 A | 5/1995 | Whittaker | |
| 5,437,918 A | 8/1995 | Taniguchi | |
| 5,441,515 A | 8/1995 | Khosravi | |
| 5,458,653 A | 10/1995 | Davidson | |
| 5,470,334 A | 11/1995 | Ross et al. | |
| 5,522,817 A | 6/1996 | Sander et al. | |
| 5,525,706 A * | 6/1996 | Gruber et al. ............... 528/354 |
| 5,527,337 A * | 6/1996 | Stack et al. ................. 606/198 |
| 5,527,341 A | 6/1996 | Gogolewski et al. | |
| 5,562,704 A | 10/1996 | Tamminmaki et al. | |
| 5,571,193 A | 11/1996 | Kampner | |
| 5,571,204 A | 11/1996 | Nies | |
| 5,633,002 A | 5/1997 | Stricker | |
| 5,634,936 A | 6/1997 | Linden | |
| 5,660,846 A | 8/1997 | Cheikh | |
| 5,670,161 A | 9/1997 | Healy | |
| 5,690,671 A | 11/1997 | McGurk | |

(Continued)

FOREIGN PATENT DOCUMENTS

DE    39 36 188 A1    5/1990

(Continued)

OTHER PUBLICATIONS

Andriano, et al., 'Processing and characterization of absorbable polyactide polymers for use in surgical implants,' *Journal of Applied Biomaterials*, 5(2):133-140 (1994).

(Continued)

*Primary Examiner*—Tae H Yoon
(74) *Attorney, Agent, or Firm*—Kilpatrick Stockton LLP

(57) ABSTRACT

The rate of degradation of polymers and polymer blends containing (poly) lactic acid can be increased and controlled by the inclusion of up to 10% (typically less than 1%) by weight of specific additives such as lauric acid or a derivative thereof such as the anhydride.

14 Claims, 10 Drawing Sheets

U.S. PATENT DOCUMENTS

Figure 1:
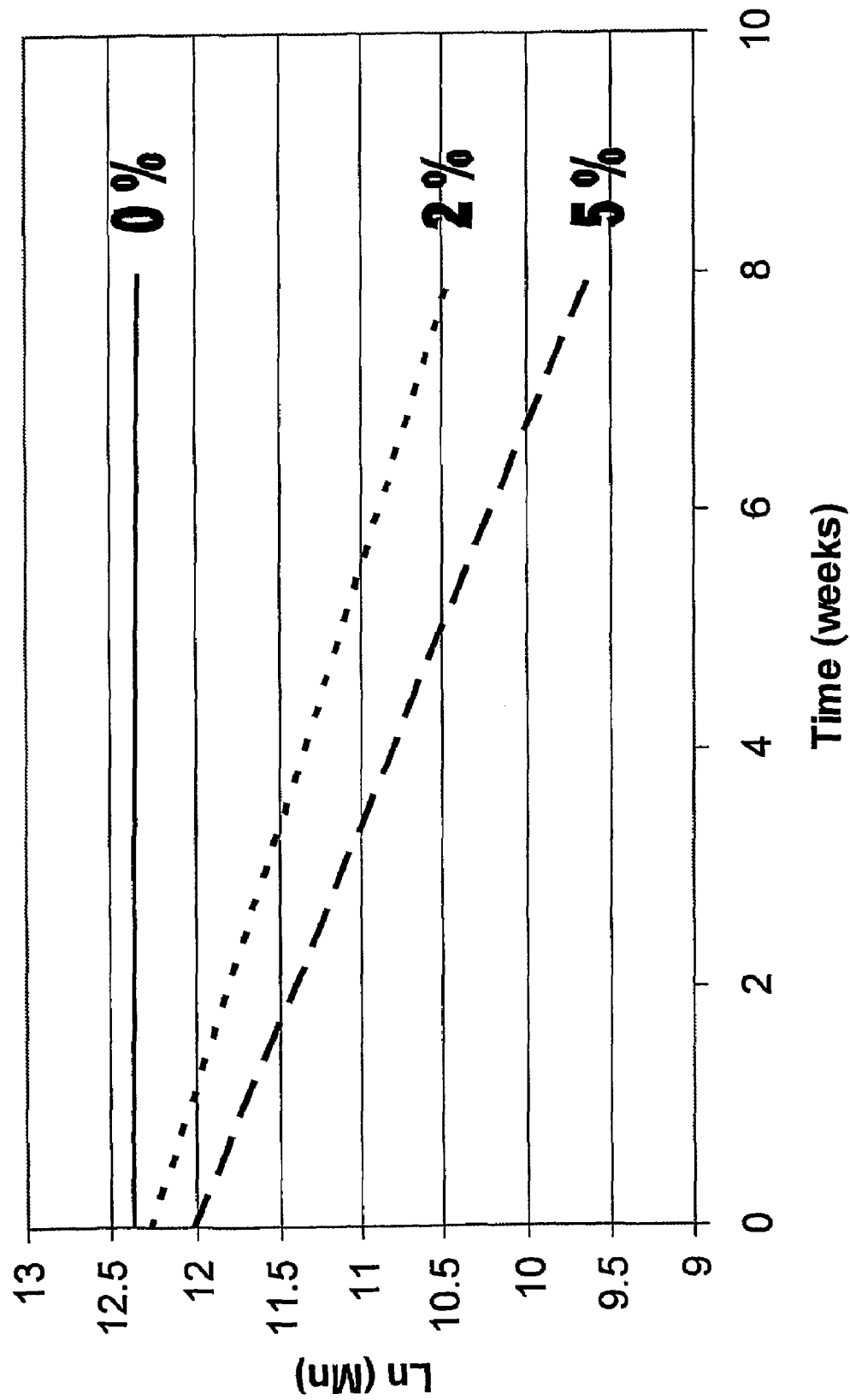

| | | | |
|---|---|---|---|
| 5,695,467 | A | 12/1997 | Stahelin |
| 5,716,410 | A | 2/1998 | Wang et al. |
| 5,716,413 | A | 2/1998 | Walter et al. |
| 5,733,330 | A | 3/1998 | Cox |
| 5,760,118 | A | 6/1998 | Sinclair |
| 5,766,239 | A | 6/1998 | Cox |
| 5,766,618 | A | 6/1998 | Laurencin et al. |
| 5,792,400 | A | 8/1998 | Talja et al. |
| 5,834,582 | A | 11/1998 | Sinclair |
| 5,837,276 | A | 11/1998 | Carnevale |
| 5,853,639 | A | 12/1998 | Kawakami et al. |
| 5,893,850 | A | 4/1999 | Cachia |
| 5,904,658 | A | 5/1999 | Niederauer et al. |
| 5,908,918 | A | 6/1999 | Chen |
| 5,935,172 | A | 8/1999 | Ochoa et al. |
| 5,968,092 | A | 10/1999 | Buscemi |
| 5,977,204 | A | 11/1999 | Boyan et al. |
| 5,980,564 | A | 11/1999 | Stinson |
| 5,997,580 | A | 12/1999 | Mastrorio et al. |
| 6,001,100 | A | 12/1999 | Sherman et al. |
| 6,001,101 | A | 12/1999 | Augagneur et al. |
| 6,005,161 | A | 12/1999 | Brekke et al. |
| 6,013,080 | A | 1/2000 | Khalili |
| 6,022,352 | A | 2/2000 | Vandewalle |
| 6,071,312 | A | 6/2000 | Lampe et al. |
| 6,077,989 | A | 6/2000 | Kandel et al. |
| 6,113,624 | A | 9/2000 | Bezwada et al. |
| 6,136,369 | A | 10/2000 | Leitao et al. |
| 6,150,497 | A | 11/2000 | Sastry et al. |
| 6,160,084 | A | 12/2000 | Langer et al. |
| 6,162,225 | A | 12/2000 | Gertzman et al. |
| 6,187,008 | B1 | 2/2001 | Hamman |
| 6,203,573 | B1 | 3/2001 | Walter et al. |
| 6,248,108 | B1 | 6/2001 | Tormala |
| 6,248,430 | B1 * | 6/2001 | Toyoda et al. ............... 428/213 |
| 6,281,262 | B1 | 8/2001 | Shikinami |
| 6,283,973 | B1 | 9/2001 | Hubbard et al. |
| 6,293,950 | B1 | 9/2001 | Lynch et al. |
| 6,303,697 | B1 | 10/2001 | Yuan et al. |
| 6,315,788 | B1 | 11/2001 | Roby |
| 6,344,496 | B1 | 2/2002 | Niederauer et al. |
| 6,375,465 | B1 | 4/2002 | Engman et al. |
| 6,423,062 | B2 | 7/2002 | Enayati |
| 6,425,923 | B1 | 7/2002 | Stalcup et al. |
| 6,436,136 | B1 | 8/2002 | Flodin et al. |
| 6,468,277 | B1 | 10/2002 | Justin et al. |
| 6,471,707 | B1 | 10/2002 | Miller et al. |
| 6,503,278 | B1 | 1/2003 | Pohjonen |
| 6,511,511 | B1 | 1/2003 | Slivka et al. |
| 6,514,286 | B1 | 2/2003 | Leatherbury et al. |
| 6,565,606 | B1 | 5/2003 | Bruce et al. |
| 6,605,090 | B1 | 8/2003 | Trieu et al. |
| 6,652,582 | B1 | 11/2003 | Stinson |
| 6,719,935 | B2 | 4/2004 | Tunc |
| 6,783,712 | B2 | 8/2004 | Slivka et al. |
| 6,827,743 | B2 | 12/2004 | Eisermann et al. |
| 6,841,111 | B2 | 1/2005 | Rickner et al. |
| 6,881,766 | B2 | 4/2005 | Hain |
| 6,908,466 | B1 | 6/2005 | Bonutti et al. |
| 6,916,321 | B2 | 7/2005 | TenHuisen et al. |
| 7,033,603 | B2 | 4/2006 | Nelson et al. |
| 7,261,716 | B2 | 8/2007 | Strobel et al. |
| 7,261,734 | B2 | 8/2007 | Gellman et al. |
| 7,268,205 | B2 | 9/2007 | Williams et al. |
| 7,270,813 | B2 | 9/2007 | Shimp et al. |
| 2002/0022588 | A1 * | 2/2002 | Wilkie et al. .................... 514/2 |
| 2002/0029043 | A1 | 3/2002 | Ahrens et al. |
| 2002/0123751 | A1 | 9/2002 | Fallin |
| 2002/0150775 | A1 * | 10/2002 | Ishikawa et al. ............ 428/458 |
| 2002/0160032 | A1 | 10/2002 | Long et al. |
| 2003/0045941 | A1 | 3/2003 | Lewallen |
| 2003/0114937 | A1 | 6/2003 | Leatherbury et al. |
| 2003/0125745 | A1 | 7/2003 | Tseng et al. |
| 2003/0236573 | A1 | 12/2003 | Evans et al. |
| 2004/0019386 | A1 | 1/2004 | Ferree |
| 2004/0106734 | A1 | 6/2004 | Rose |
| 2004/0156878 | A1 | 8/2004 | Rezania et al. |
| 2004/0193154 | A1 | 9/2004 | Leatherbury et al. |
| 2004/0241203 | A1 | 12/2004 | Shakesheff et al. |
| 2004/0242722 | A1 | 12/2004 | Rose |
| 2004/0258732 | A1 | 12/2004 | Shikinami |
| 2004/0260398 | A1 | 12/2004 | Kelman |
| 2004/0265385 | A1 | 12/2004 | West |
| 2004/0267263 | A1 | 12/2004 | May |
| 2005/0008672 | A1 | 1/2005 | Winterbottom et al. |
| 2005/0013793 | A1 | 1/2005 | Beckman et al. |
| 2005/0085313 | A1 | 4/2005 | Nishitani |
| 2005/0107886 | A1 | 5/2005 | Crabtree et al. |
| 2005/0159812 | A1 | 7/2005 | Dinger, III et al. |
| 2005/0165128 | A1 | 7/2005 | Cohn et al. |
| 2005/0177245 | A1 | 8/2005 | Leatherbury et al. |
| 2005/0209705 | A1 | 9/2005 | Niederauer et al. |
| 2005/0240281 | A1 | 10/2005 | Slivka et al. |
| 2006/0067973 | A1 | 3/2006 | Schachter |
| 2006/0136071 | A1 | 6/2006 | Maspero et al. |
| 2006/0178748 | A1 | 8/2006 | Dinger, III et al. |
| 2006/0188547 | A1 | 8/2006 | Bezwada |
| 2006/0200150 | A1 | 9/2006 | Homaki et al. |
| 2006/0247610 | A1 | 11/2006 | Lanphere et al. |
| 2006/0263335 | A1 | 11/2006 | France et al. |
| 2007/0041950 | A1 | 2/2007 | Leatherbury et al. |
| 2007/0043376 | A1 | 2/2007 | Leatherbury et al. |
| 2007/0128154 | A1 | 6/2007 | Hadba et al. |
| 2007/0134305 | A1 | 6/2007 | Zilberman |
| 2007/0191963 | A1 | 8/2007 | Winterbottom et al. |
| 2007/0240281 | A1 | 10/2007 | Slivka et al. |
| 2007/0299156 | A1 | 12/2007 | Brown |

FOREIGN PATENT DOCUMENTS

| | | |
|---|---|---|
| DE | 42 26 465 A1 | 2/1993 |
| DE | 42 20 216 C1 | 1/1994 |
| EP | 0 204 931 B2 | 12/1986 |
| EP | 0 321 389 A1 | 6/1989 |
| EP | 0 401 844 B1 | 12/1990 |
| EP | 0 439 892 A2 | 8/1991 |
| EP | 0 595 956 | 5/1994 |
| EP | 0 635 274 A2 | 1/1995 |
| EP | 0 531 487 B1 | 1/1996 |
| EP | 0 711 534 A1 | 5/1996 |
| EP | 0 751 165 A | 1/1997 |
| EP | 0 805 175 A1 | 1/1997 |
| EP | 0 803 521 A1 | 10/1997 |
| EP | 0 806 283 A2 | 11/1997 |
| EP | 1 056 487 | 12/2000 |
| EP | 1 136 510 | 9/2001 |
| EP | 1 093 774 B1 | 6/2002 |
| EP | 0 815 809 B1 | 3/2004 |
| GB | 807589 | 1/1959 |
| GB | 2319479 | 5/1998 |
| JP | 2169612 | 6/1990 |
| JP | 8196617 | 8/1996 |
| JP | 9040761 | 2/1997 |
| JP | 9095606 | 4/1997 |
| JP | 9221539 | 8/1997 |
| JP | 9234241 | 9/1997 |
| JP | 9272790 | 10/1997 |
| JP | 10176039 | 6/1998 |
| KR | 141988 B1 | 6/1998 |
| WO | WO 1984/04311 | 11/1984 |
| WO | WO 1990/003768 | 4/1990 |
| WO | WO 1993/01773 | 2/1993 |
| WO | WO 1995/034331 A1 | 12/1995 |
| WO | WO 1997/005193 A1 | 2/1997 |

| WO | WO 1998/026814 A1 | 6/1998 |
| WO | WO 1999/011297 A2 | 3/1999 |
| WO | WO 1999/22770 | 5/1999 |
| WO | WO 00/01426 | 1/2000 |
| WO | WO 01/46501 | 6/2001 |
| WO | WO 2001/096105 A2 | 12/2001 |
| WO | WO 02/00137 | 1/2002 |
| WO | WO 2002/076725 | 10/2002 |
| WO | WO 03/004071 | 1/2003 |
| WO | WO 03/064531 | 8/2003 |
| WO | WO 2003/064531 A1 | 8/2003 |
| WO | WO 2004/011054 | 2/2004 |
| WO | WO 2004/071356 A2 | 8/2004 |
| WO | WO 2005/014718 A1 | 2/2005 |
| WO | WO 2005/085313 A1 | 9/2005 |
| WO | WO 2006/053936 | 5/2006 |
| WO | WO 2006/064025 | 8/2006 |
| WO | WO 2007/020430 | 2/2007 |
| WO | WO 2007/020432 | 2/2007 |
| WO | WO 2007/065074 A2 | 6/2007 |
| WO | WO 2007/084609 A2 | 7/2007 |

OTHER PUBLICATIONS

Asano, et al., 'In vivo characteristics of low molecular weight copoly(D,L-lactic acid) formulations with controlled release of LH-RH agonist,' *Biomaterials*, 10(8):569-573 (1989).

Barca, et al., 'Resorbable poly-L-lactic acid mini-staples for the fixation of Akin osteotomies,' *The Journal of Foot and Ankle Surgery*, 36(2):106-111 (1997).

Bertrand, et al., 'Biocompatbility Aspects of New Stent Technology, *JACC*, 32(3):562-571 (1998).

Celikkaya, et al., 'Poly(DL-lactide)/Poly(ethylene glycol) Copolymer Particles. I. Preparation and Characterization,' *Journal of Applied Polymer Science*, 61:1439-1446 (1996).

Frenger, 'Biomedical Uses of Shape Memory Polymers,' *Biomed. Sci. Instrum.*, 29:47-50 (1993).

Fukuzaki, et al., 'Synthesis of copoly(D,L-Lactic acid) with relatively low molecular weight and in cirto degradation, Japan Atomic Energy Research Intitute, Gunma, Jpn, European Polymer Journal, 25(10):1019-1026 (1989).

Giardino, et al., 'Experimental evaluation of a resorbable intramedullary plug for cemented total hip replacement,' *Biomaterials*18(13):907-913 (1997).

Gautier, et al., 'Poly(á-hydroxyacids) for application in the spinal cord: Resorbability and biocompatability with adult rate Schwann cells and spinal cord,' *Journal of Biomedical Materials Research*, 42(4):642-654 (1998).

Haers, et al., 'Biodegradable polyactide plates and screws in orthognathic surgery,' *Journal of Cranio-Maxillofacial Surgery*, 26(2):87:91 (1998).

L. L. Hench, et al., 'Bioactive materials: The potential for tissue regeneration,' *J. Biomed. Materials Research*, 41(4):511-518 (1998).

D. Hull and T. W. Clyne, 'An introduction to composite materials,' Second Edition, Cambridge University Press, Table of Contents, 8 pages.

Hyon, et al., 'Effects of residual monomer on the degradation of DL-lactide polymer,' Hyon, Jamshidi & Ikada, *Polymer International*, 46:196-202 (1998).

Kaitian, et al., 'Poly(D,L-Lactic Axcid) Homopolymers: Synthesis and Characterization,' *Turkish Journal of Chemistry*, 20:43-53 (1996).

Kister, et al., 'Effects of morphology, conformation and configuration on the IR and Raman spectra of various poly(lactic acid)s,' *Polymer*, 39(2): 267-273 (1998).

Koelling, et al., 'In vitro real-time aging and characterization of poly(L/D-lactic acid),' *Proceedings of the 1997 16th Southern Biomedical Engineering Conference* (Cat. No. 97$^{TH}$8270), pp. 197-201.

Kontio, et al., 'Fibrous wound repair associated with biodegradable poly-L/D/-lactide copolymers implants: study of the expression of tenascin and cellular fibronectin,' *Journal of Materials Science-Materials in Medicine*, 9:10:603-609 (1998).

Kricheldorf, et al., 'Polyactones: 32. High-molecular weight polyactides by ring-opening polymerization with dibutylmagnesium or butylmagnesium chloride,' *Polymer*, 36(15):2995-3003.

Losken, et al., 'Memory of DL-polyactic acid biodegradable plates,' *Ann. Plast. Surg.*, 32(6):606-611 (1994).

MacDonald, et al., 'Enzymatic degradability of poly(lactide): Effects of chain stereochemistry and material crystallinity, ' *Macromolecules*, 29(23):7356-7361 (1996).

Mainil-Varlet, et al., 'Effect of in vivo and in vitro degradation on molecular and mechanical properties of various low-molecular weight polylactides,' *Journal of Biomedical Materials Research*, 36(3):360-380 (1997).

Matsumura, et al., 'Novel ring opening polymerization of lactide by lipase,' *Macromol. Symp.*, 130:285-304 (1998).

Morita, et al., 'Intravitreous delivery of dexamethasone sodium m-sulfobenzoate from poly(DL-lactic acid) implants,' *Biological & Pharmaceutical Bulletin*, 21(2):188-190 (1998).

Okihara, et al., 'crystal structure of stereocomplex of poly(L-lactide) and poly(D-lactide), *Journal of Macromolecular Science-Physics*, B30(1-2):119-140 (1991).

Okuzaki, et al., Mechanical Properties and Structure of the Zone-Drawn Poly(L-lactic acid) Fibers, *Journal of Polymer Science, Part B, Polymer Physics*, 37:991-996 (1999).

Oriented Polymer materials, Edited by Stoyko Fakirov, published by Huthig & Wepf Verlag Zug, Heidelberg, Oxford CT/USA, Table of Contents pp. v, viii, ix-xix (1996).

Penning, et al., 'Preparation and properties of adsorbable fibers from L-lactide copolymers,' *Polymer*, 34(5):942-951 (1993).

Pitt, et al., 'Modification of the rates of chain cleavage of poly(ϵ-caprolactone) and related polyesters in the solid state,' *Journal of Controlled Releaase*, 4:283-292 (1987).

Pitto, et al., "Compaison of fixation of the femoral component without cement and fixation with use of a bone-vacuum cementing technique for the prevention of fat embolism during total hip arthoplaasty," *J. Bone Joint Surg.*, 81-A(6):831-843 (1999).

Rak, et al., 'The preparation and characterization of poly(DL-lactic acid) for use as a biodegradable drug carrier,' Liverpool Polytech., Liverpool, UK, *Pharmaceutica Acta Helvetiae*, 60:(5-6):162-169 (1985).

Ristic, et al., 'An investigation of synthesis and degradation of poly(D,L-lactide) and controlled release of albumin from biodegradable poly(D,L-lactide) cylinders,' ICheaP-2, the second Italian conference on chemical and process engineering, Florence, pp. 559-563 (1995).

Schliephake, et al., 'Reconstruction of the mandible by prefabricated autogenous bone grafts,' *Int. J. Oral Maxillofac. Surg.*, 26:244-252 (1997).

Stahelin, et al., 'Clinical degradation and biocompatibility of different biooabsorbable interference screws: a report of six cases,' *Arthoscopy: The Journal of Arthroscopic & Related Surgery*, 13(2):238-244 (1997).

Steendam, et al., 'The role of elastic relaxation in drug delivery from poly(DL-lactic acid) based tablets. A shape memory phenomenon,' *Proceedings of the International Symposium on Controlled Release of Bioactive Materials*, 25:128-129 (1998).

Stevels, et al., 'Blends van blok copolymeren die een poly(L-lactide) of poly(D-lactide) blok bevatten,' Biomedical Science and Engineering Meeting, pp. 107-110 (1994).

Tagil, "Thesis - The morselized and impacted bone graft animal experiments on proteins, imaction and load," *Acta Orthop. Scand. Suppl.*, 290:1-40 (2000).

Temenoff and Mikos, "Injectable biodegradable materials for orthopedic tissue engineering," *Biomaterials*, 21:2405-2412 (2000).

Tscgakaloff, et al., 'Degradation kinetics of biodegradable DL-polyactic acid biodegradable implants depending on the site of implantation,' *International Journal of Oral and Maxillofacial Surgery*, 23(6 Pt2):443-445 (1994).

Tsuji, et al., 'Sterocomplex formation between enantiomeric poly(lactic acid). VIII. Complex fibers spun from mixed solution of poly(D-lactic acid) and poly(L-lactic acid), *Journal of Applied Polymer Science*, 51(2):337-344 (1994).

J. West, J. Hubbell, 'Bioactive Polymers, Synthetic biodegradable polymer scaffolds,' Chapter 5, pp. 83-95, Anthony Atala and David J. Mooney, Editors; Joseph P. Vacanti and Robert Langer, Associate Editors, Birkhauser (1997).

D. Wheeler, et al., 'Effect of bioactive glass particle size on osseous regeneration of cancellous defects,' *J. Biomed. Materials Research*, 41(4):527-533 (1998).

Zegzula, et al., 'Bone Formation with Use of rgBMP-2 (Recombinant Human Bone Morphogenetic Protein-2,' *The Journal of Bone and Joint Surgery*, 79:1778-1790 (1997).

Zhang, 'Biodegradable lactide polymers: synthesis, degradation, and controlled drug release properties (drug release), Queen's University at Kingston, Canada, vol. 55/01-B Dissertation Abstracts International, p. i-xv, 1-179 (Oct. 1993).

Structure and Properties of Orientated Polymers, Ed. I. M. Ward, Department of Physics, University of ELads, England, a Halsted Press Book, John Wiley & Sons, New York-Toronto (1975) Table of Contents.

Gupta, et al., 'Poly(lactic acid) fiber: An overview Progress in Polymer Science, Pergamon Press, Oxford, GB, 32(4):455-482 (2007).

Daniels, et al., 'Mechanical properties of biodegradable polymers and composites proposed for internal fixation of bone,' *J. Applied Biomaterials*, 1:57-78 (1990).

Dauner, et al., 'Resorbable continuous-fiber reinforced polymers for osteosynthesis,' *J. Materials Science Materials in Medicine*, 9:173-179 (1998).

Eling, et al., 'Biodegradable Materials of Poly(L-Lactic Acid): 1. Melt-Spun and Solution-Spun Fibers,' *Polymer*, 23:1587-1593 (1982).

Fambri, et al., 'Biodegradable fibers of poly(l-lactic acid) produced by melt spinning,' *Polymer*, 38:79-85 (1997).

Gogolewsji, et al., 'Resorbable materials of poly(L-lactide). II Fibers spun from solutions of poly(L-lactide) in good solvents,' *J. Appl. Polymer Sci.*, 28:1045-1061 (1983).

\* cited by examiner

BIODEGRADABLE POLYMER SYSTEMS

This invention relates to biodegradable polymeric materials, particularly to bioresorbable materials and to artifacts made therefrom.

Poly (lactic acid), also commonly known as PLA has been widely used, either as the D-isomer or the mixed DL-form, for the manufacture of implant materials where bioresorbabilty is a required property. Although PLA is biodegradable it will normally take from 3 to 5 years to be fully resorbed. A further disadvantage is that although it takes 3 to 5 years to fully degrade the mechanical strength of implants made from poly (L-lactic acid) (PLLA) will be lost within a fifth of that time The in vivo degradation of PLA takes place predominately via an autocatalysed hydrolytic scission of the ester groups in the polymer chain according to the reaction:

$\sim$COO$\sim$ + H$_2$O $\xrightarrow{\text{COOH}}$ $\sim$COOH + HO$\sim$

Attempts to increase the carboxylic acid functionality of the polymeric material and, hence, increase the rate of degradation of PLA have been reported in the literature ("*Modification of the rates of chain cleavage of poly ($\epsilon$-caprolactone) and related polyesters in the solid state*", *Journal of Controlled Release*, 4, (1987) pp 283-292.) in which samples of PLA have been contacted with carboxyl group-containing materials such as oleic acid. No effect on the rate of degradation was reported. The effect of lactic acid monomer in PLA has also been investigated and reported ("*Effects of residual monomer on the degradation of DL-lactide polymer*" Hyon, Jamshidi & Ikada, *Polymer International*, 46 (1998), pp 196-202). However, it was found that the added monomer rapidly leached out of the polymer. Polymer blends containing 15 weight percent lactic acid exhibited a total weight loss of about 15% within the first week of a 10 week study and very little further loss in the remaining weeks.

In U.S. Pat. No. 5,527,337 there is disclosed a biodegradeable stent formed from lactide polymers wherein, inter alia, an excipient such as ctric acid or fumaric acid can be incorporated during the polymer processing. Other additives which which can be used to accelerate stent degradation which are not acids themselves are also disclosed including the tertiary butyl ester of lauric acid and the ditertiary butyl ester of fumaric acid.

U.S. Pat. No. 6,248,430 describes a laminate, for use in the manufacture of molded products for agricultural or civil engineering purposes. The laminate consists of a base layer comprising a lactic acid-based polymer having a degradation accelerator incorporated therein and a barrier layer which comprises a lactic acid based polymer having a lactide content of not more than 0.1% by weight, for the purpose of preventing the accelerator from leaking from the base polymer. The lactic acid-based polymer comprises a polyester made of polylactic acid component, lactic acid component dicarboxylic acid component, diol component and/or polyether component or a mixture thereof. Examples of materials useful as an accelerator include organic acids such as lactic, glyceric, tartaric, citric, lauric, stearic, oleic, succinic, adipic sebacic, benzoic and phthalic acids. The disclosure shows that the accelerators are incorporated during the polymer forming process.

Although it is known in the prior art to attempt to increase the carboxyl functionality by using acid based accelerators it has been a problem to retain such accelerators within the polymer mass for a sufficient period of time to allow control of the rate of degradation. The prior attempts to control degradation require either the use of physical barrier layers to retain the accelerator or the use of complex polymer systems.

We have now found that it is possible to control the rate of degradation of lactic acid polymers by homogeously blending certain additives which are both fully miscible with PLA and will not leach out. The blending process is simple and results in stable polymer blends which can be readily thermoformed, such as by injection molding to form implantable medical devices which will both maintain their physical strength yet biodegrade in a predictable manner.

Thus in accordance with the present invention there is provided an implantable, biodegradable medical device formed from a homogeneous polymer blend comprising a poly lactic acid in admixture, in an amount of not more than 10% by weight of the polymer blend, with an additive which is an acid or a derivative thereof selected from the group consisting of hexanoic acid, octanoic acid, decanoic acid, lauric acid, myristic acid, crotonic acid, 4-pentenoic acid, 2-hexenoic acid, undecylenic acid, petroselenic acid, oleic acid, erucic acid, 2,4-hexadienoic acid, linoleic acid, linolenic acid, benzoic acid, hydrocinnamic acid, 4-isopropylbenzoic acid, ibuprofen, ricinoleic acid, adipic acid, suberic acid, phthalic acid, 2-bromolauric acid, 2,4-hydroxydodecanoic acid, monobutyrin, 2-hexyldecanoic acid, 2-butyloctanoic acid, 2-ethylhexanoic acid, 2-methylvaleric acid, 3-methylvaleric acid, 4-methylvaleric acid, 2-ethylbutyric acid, trans-beta-hydromuconic acid, isovaleric anhydride, hexanoic anhydride, decanoic anhydride, lauric anhydride, myristic anhydride, 4-pentenoic anhydride, oleic anhydride, linoleic anhydride, benzoic anhydride, poly(azelaic anhydride), 2-octen-1-yl succinic anhydride and phthalic anhydride.

The additive concentration is chosen such that it must be fully miscible with the polymer blend and should not leach out of the polymer.

As used herein the term "fully miscible" means that when an 0.5 mm thick sheet of the polymer blend is visually inspected the sheet is either uniformly transparent or, if the sheet is opaque, the opacity is uniform.

As used herein the term "not leach out of the polymer" is defined such that when a thin (thickness <1 mm) sample is immersed in an excess of PBS (Phosphate buffer solution), at least half of the added additive remains in the sample after 1 week.

Aptly the polymer blend will contain not more than 5%, more preferably not more than 2%, by weight of the additive and typically the blend will contain not more than 1% by weight of the additive. Preferred blends will contain not more than 2%, more preferably not more than 1%, by weight of the blend of lauric acid or a derivative thereof.

The amount of the additive chosen will also depend upon the rate of degradation desired. In vivo degradation occurs firstly by hydrolytic scission of the ester groups resulting in the formation of units of increasingly smaller molecular weight until only substantially lactic acid monomer remains. Thereafter, the lactic acid is metabolized and absorbed into the body. It is only in the last stages of degradation that mass loss occurs.

The mechanical properties of the implant are retained in the early stages of degradation, even though the molecular weight may decrease markedly. Eventually a critical molecular weight is reached and the implant will cease to have any useful mechanical strength yet will not have degraded sufficiently for resorption to occur.

We have found that a preferred additive for use in the invention is lauric acid. This may be employed as the acid per se or, if desired, as a derivative, for example as the anhydride.

By the use of the blends for the present invention not only may the total rate of degradation and resorption be controlled but it is possible to control the rate of degradation in order to optimize the mechanical properties. In many, surgical procedures, where the implant is required to provide temporary support until the condition has been treated by the body's own natural repair or rebuilding activity. When the support provided by the implant is no longer required it is often desirable that the strength of the implant be markedly reduced.

Thus in accordance with a further embodiment of the present invention there is provided an implantable, biodegradable medical device having predetermined strength retention comprising a homogeneous blend of a polylactic acid in admixture with an additive as hereinabove defined, in an amount, calculated as weight percent, based on the weight of the total polymer blend represented by the following equation:

$$\% \text{ additive} = M_{nA} * 100 * \left\{ \left[ \frac{Ln\left(\frac{M_{n0}}{M_{ns}}\right) - tk_1}{tk_2} \right]^2 - \frac{1}{M_{n0}} \right\}$$

where:—
$M_{n0}$=polymer initial molecular weight
$M_{ns}$=Mn at which the polymer looses strength
$M_{nA}$=molecular weight of the acid
t=Duration (weeks) that strength retention is required
$k_1$=constant 1
$k_2$=constant 2

The constants $k_1$ and $k_2$ are the slope and intercept of a graph of the degradation rate of a blend against the square root of the total number of COOH groups in the blend. The degradation rate of a blend is the slope of a graph of Ln(Mn) against degradation time in weeks.

The degradation rates of the additives employed as 2% by weight component in a polylactic acid blend in the present invention are shown in the following table:

| Additive | Degradation rate |
| --- | --- |
| Hexanoic acid | −0.0565 |
| Octanoic acid | −0.0448 |
| Decanoic acid | −0.0472 |
| Lauric acid | −0.0326 |
| Myristic acid | −0.0281 |
| Crotonic acid | −0.0489 |
| 4-Pentenoic acid | −0.0567 |
| 2-Hexenoic acid | −0.0713 |
| Undecylenic acid | −0.07 |
| Petroselenic acid | −0.0542 |
| Oleic acid | −0.0442 |
| Erucic acid | −0.0315 |
| 2,4-Hexadienoic acid | −0.0618 |
| Linoleic acid | −0.0488 |
| Linolenic acid | −0.0589 |
| Benzoic acid | −0.0798 |
| Hydrocinnamic acid | −0.0737 |
| 4-Isopropylbenzoic acid | −0.0728 |
| Ibuprofen | −0.051 |
| Ricinoleic acid | −0.061 |
| Adipic acid | −0.0373 |
| Suberic acid | −0.0311 |
| Phthalic acid | −0.0855 |
| 2-Bromolauric acid | −0.0769 |
| 2,4-Hydroxydodecanoic acid | −0.0318 |
| Monobutyrin | −0.0347 |
| 2-Hexyldecanoic acid | −0.0339 |
| 2-Butyloctanoic acid | −0.0467 |
| 2-Ethylhexanoic acid | −0.0473 |
| 2-Methylvaleric acid | −0.0411 |
| 3-Methylvaleric acid | −0.0587 |
| 4-Methylvaleric acid | −0.0553 |
| 2-Ethylbutyric acid | −0.053 |
| Trans-beta-hydromuconic acid | −0.039 |
| Isovaleric anhydride | −0.0628 |
| Hexanoic anhydride | −0.0919 |
| Decanoic anhydride | −0.0807 |
| Lauric anhydride | −0.0698 |
| Myristic anhydride | −0.0626 |
| 4-Pentenoic anhydride | −0.0888 |
| Oleic anhydride | −0.0504 |
| Linoleic anhydride | −0.0696 |
| Benzoic anhydride | −0.0817 |
| Poly(azelaic anhydride) | −0.0784 |
| 2-Octen-1-yl succinic anhydride | −0.1012 |
| Phthalic anhydride | −0.0841 |

A further embodiment of the present invention provides the provision of an additive which not only will control the rate of degradation but will delay the onset of the degradation process. This delay may be achieved, aptly by the use of additives which are convertible to the acidic form of the additive. Suitable derivatives are acid anhydrides which will, in an in vivo environment hydrolyse to the corresponding acid. Preferred anhydrides include lauric anhydride and benzoic anhydride, in amounts of, aptly, not more than 5%, more aptly, not more than 2% and, typically, not more than 1% by weight of the polymer blend.

Thus specifically the present invention provides an implantable, biodegradable medical device having predetermined strength retention comprising a homogeneous blend of a polylactic acid in admixture with lauric anhydride or benzoic anhydride in an amount, calculated as weight percent, based on the weight of the total polymer blend, represented by the following equation:

$$\% \text{ additive} = M_{nA} * 100 * \left\{ \left[ \frac{Ln\left(\frac{M_{n0}}{M_{ns}}\right) - tk_1}{tk_2} \right]^2 - \frac{1}{M_{n0}} \right\}$$

where $M_{n0}$, $M_{ns}$, $M_{nA}$, $k_1$ and $k_2$ are as defined herein and t is the duration (weeks) that strength retention is required once onset of degradation has comenced The polymeric component of the polymer blends useful for the invention essentially comprise a poly lactic acid. The poly lactic acid may be present as a homopolymer or as a co-polymer, for example a co-polymer of lactic acid and glycolic acid (known as PLA/PGA co-polymer). The polymer blend may also contain other polymeric components blended therewith. Thus the blend may, in addition to the additive, consist of a blend of polylactic acid, PLA/PGA co-polymer. Other examples of suitable blend include blends of PLA or PLA/PGA co-polymer either alone or in admixture with each other, together with hydroxy apatite.

The polymer blends used for the present invention may be produced by known processes such as solution blending wherein the additive is blended directly into a solution of a polymeric component comprising PLA in, for example, chloroform. The solution blend is then dried.

The thus formed solid blend may then be formed per se into the medical device of the invention, by known processes such as compression moulding or extrusion or into components, such as fibres which may be further processed to form devices in accordance with the present invention.

Alternatively, the blends may be further blended or otherwise formulated with other materials to form medical devices in accordance with the invention. Thus the additive-containing blends may be utilized as the matrix component of a composite material which is then fabricated into a biodegradable medical device.

The medical devices of the invention are biodegradable and any implantable devices where temporary residence only is required. Examples of such devices include sutures, suture anchors, soft tissue anchors, interference screws, tissue engineering scaffolds, maxillo-facial plates, fracture fixation plates and rods.

The polymer blends themselves are believed to be novel compositions of matter.

Accordingly, the present invention further provides a polymer blend, useful for the manufacture of biodegradable medical devices comprising polylactic acid in admixture with an additive in an amount of not more than 10% by weight of the blend of at least one of hexanoic acid, octanoic acid, decanoic acid, lauric acid, myristic acid, crotonic acid, 4-pentenoic acid, 2-hexenoic acid, undecylenic acid, petroselenic acid, oleic acid, erucic acid, 2,4-hexadienoic acid, linoleic acid, linolenic acid, benzoic acid, hydrocinnamic acid, 4-isopropylbenzoic acid, ibuprofen, ricinoleic acid, adipic acid, suberic acid, phthalic acid, 2-bromolauric acid, 2,4-hydroxydodecanoic acid, monobutyrin, 2-hexyldecanoic acid, 2-butyloctanoic acid, 2-ethylhexanoic acid, 2-methylvaleric acid, 3-methylvaleric acid, 4-methylvaleric acid, 2-ethylbutyric acid, trans-beta-hydromuconic acid, isovaleric anhydride, hexanoic anhydride, decanoic anhydride, lauric anhydride, myristic anhydride, 4-pentenoic anhydride, oleic anhydride, linoleic anhydride, benzoic anhydride, poly(azelaic anhydride), 2-octen-1-yl succinic anhydride or phthalic anhydride.

Aptly the blend will comprise not more than 5% by weight of the additive and preferably no more than 2% by weight of the additive.

The present invention will be illustrated by reference to the following and accompanying drawings.

EXAMPLE 1

Blends of poly(L-lactic acid) containing lauric acid, in amounts respectively, 2% and 5% by weight of the blend, were prepared by first dry blending the solid materials and then solution blending the materials by roller mixing the solid mixture (10% by weight) with chloroform (90% by weight). After complete dissolution of the solids, the solutions were cast onto an open tray, left to dry (in a fume cupboard) at ambient temperature for 24 hours and dried for a further 24 hours under vacuum at ambient temperature. A control sample was also prepared by solution blending poly(L-lactic acid) alone with chloroform and drying the cast solution under the same conditions as the lauric acid-containing samples.

The dried cast films were then comminuted and approximately 10 gm charges of the blends were compression moulded between two sheets of mould release sheets maintained 0.5 mm apart. The charges were warmed for 5 minutes prior to moulding and fed into the mould at a temperature of 195° C., pressure of 100N over a period of 90 seconds to form sheets. The resultant sheets were observed to be transparent.

The sheets were cut into strips and subjected to simulated degradation by immersion in standard phosphate buffer solution (PBS), maintained at 37° C. for 10 weeks.

During the ten week test period samples were analysed:
  to determine molecular weight of the polymer blend (to measure the degree of degradation),
  to determine the lauric acid in the polymer (to measure the degree of leaching of the lauric acid additive),
  to determine the amount of Lactic acid in the PBS (to measure the amount of degradation products released into the PBS buffer).

Figure 2:
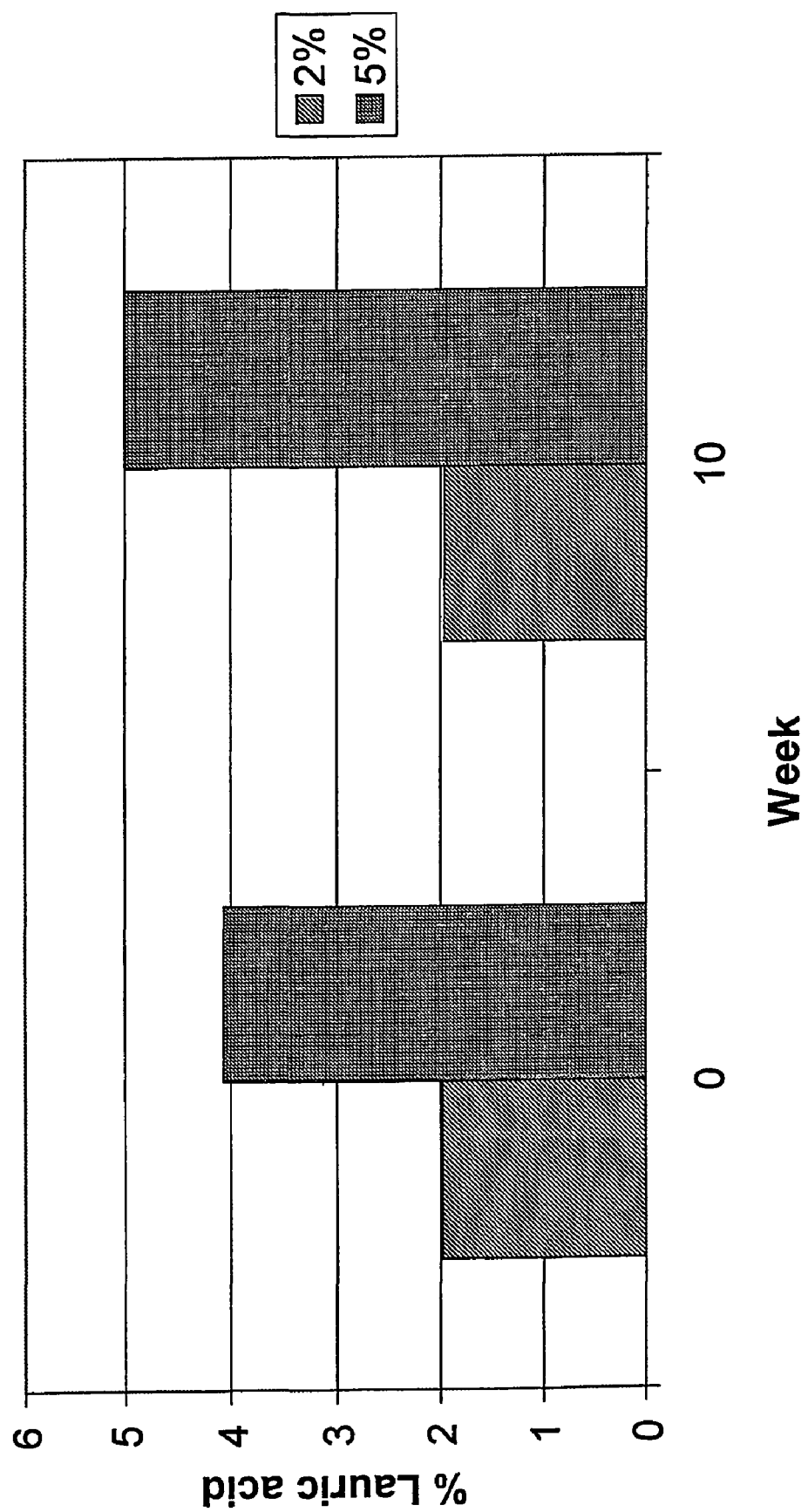

The decrease in molecular weight is reported in FIG. 1. The lauric acid remaining in the sample was determined by GC-MS. Samples were weighed (~50 mg) and 2 ml chloroform added. These were sonicated until the polymer dissolved. 20 ml of diethyl ether was added to precipitate out the polymer, this was transferred to a 50 ml volumetric and made to the mark with diethyl ether. An aliquot of the samples was vialled for analysis by GC-MS. The results for samples at weeks 0 and 10 are shown in FIG. 2.

Samples of the PBS were also analysed by HPLC to determine the amount of lactic acid (to measure resorption potential). 31 ml aliquots of the PBS were taken at each time interval and analysed under the following conditions:

| | |
|---|---|
| Mobile Phase: | 0.005N $H_2SO_4$ in water |
| Column: | Rezex 8μ 8% H. Organic Acids - 300 × 7.80 mm |
| Flow Rate: | 0.6 ml/min |
| Injection Volume: | 100 μl |
| Column Temperature: | 63° C. |
| Wavelength: | 210 nm |
| Runtime | 20 min |

Figure 3:
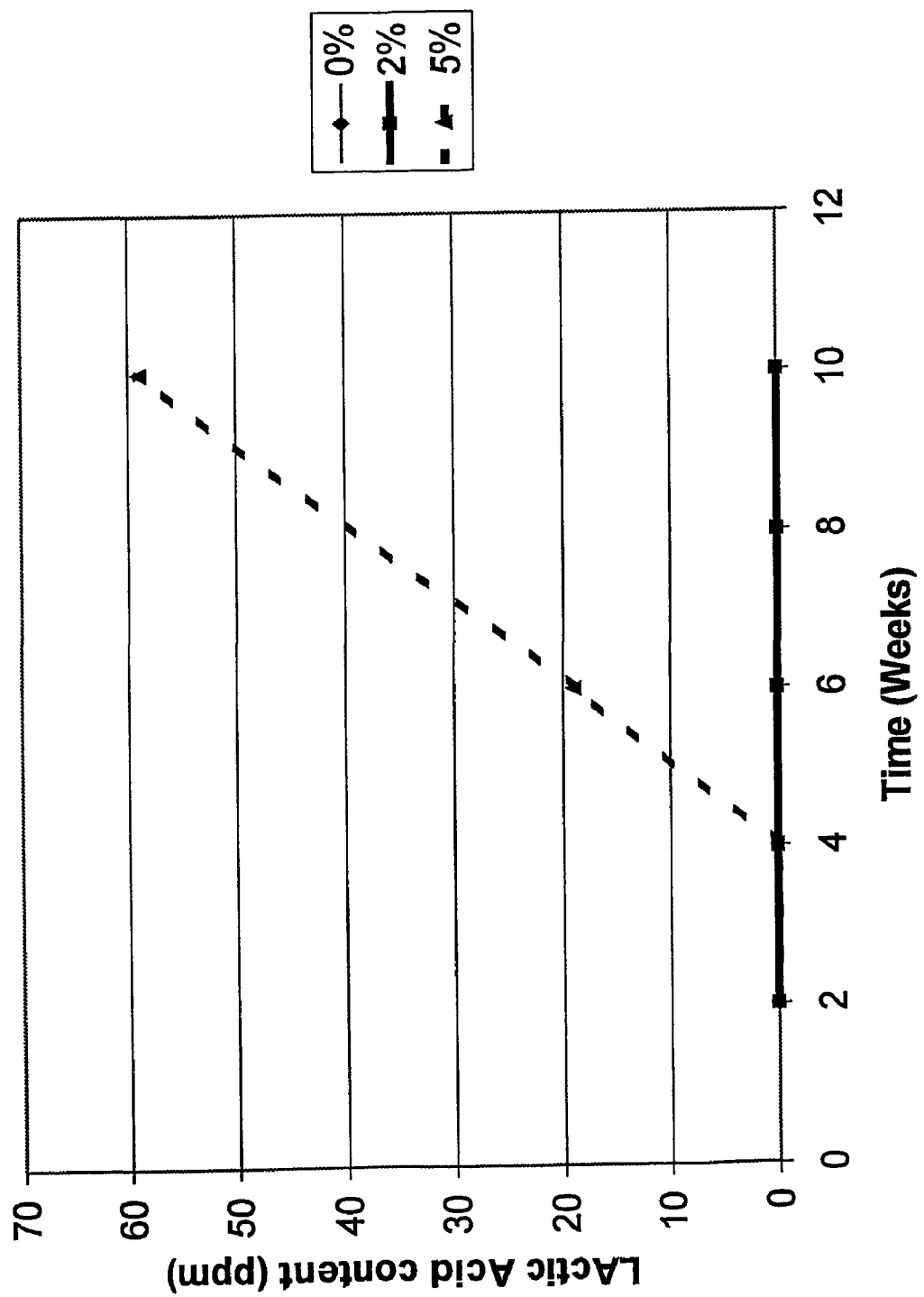

The lactic acid content of the PBS is shown in FIG. 3.

EXAMPLE 2

Blends of poly(DL-lactic acid) containing lauric acid, in amounts respectively, 2% and 4% by weight of the blend, were prepared using the method described for Example 1.

The sheets were cut into strips and subjected to simulated degradation by immersion in standard phosphate buffer solution (PBS), maintained at 37° C. for 8 weeks.

During the eight week test period samples were analysed:
  to determine molecular weight of the polymer blend (to measure the degree of degradation),
  Lactic acid (to measure the amount of degradation products released into the PBS buffer).

Figure 4:
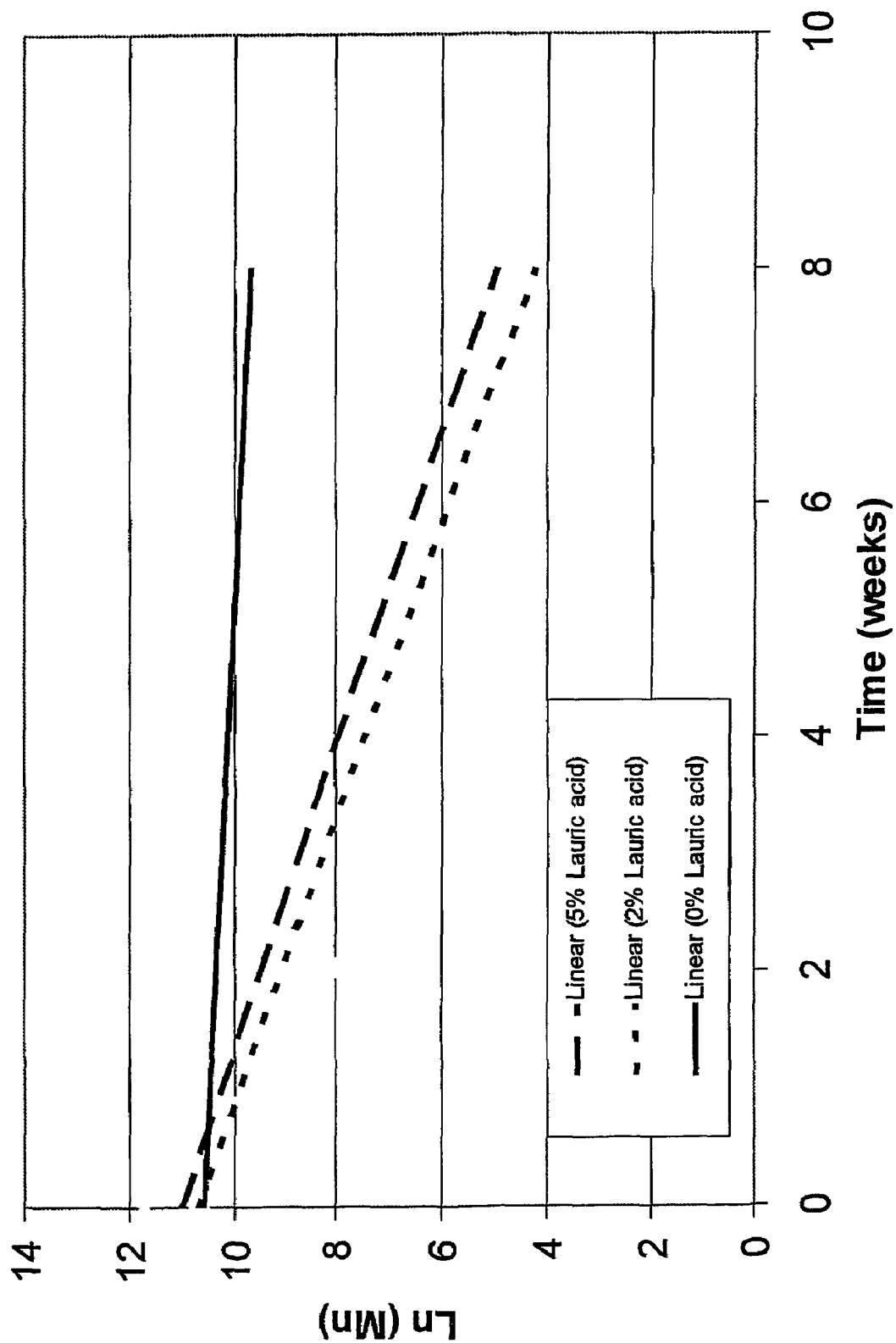
Figure 5:
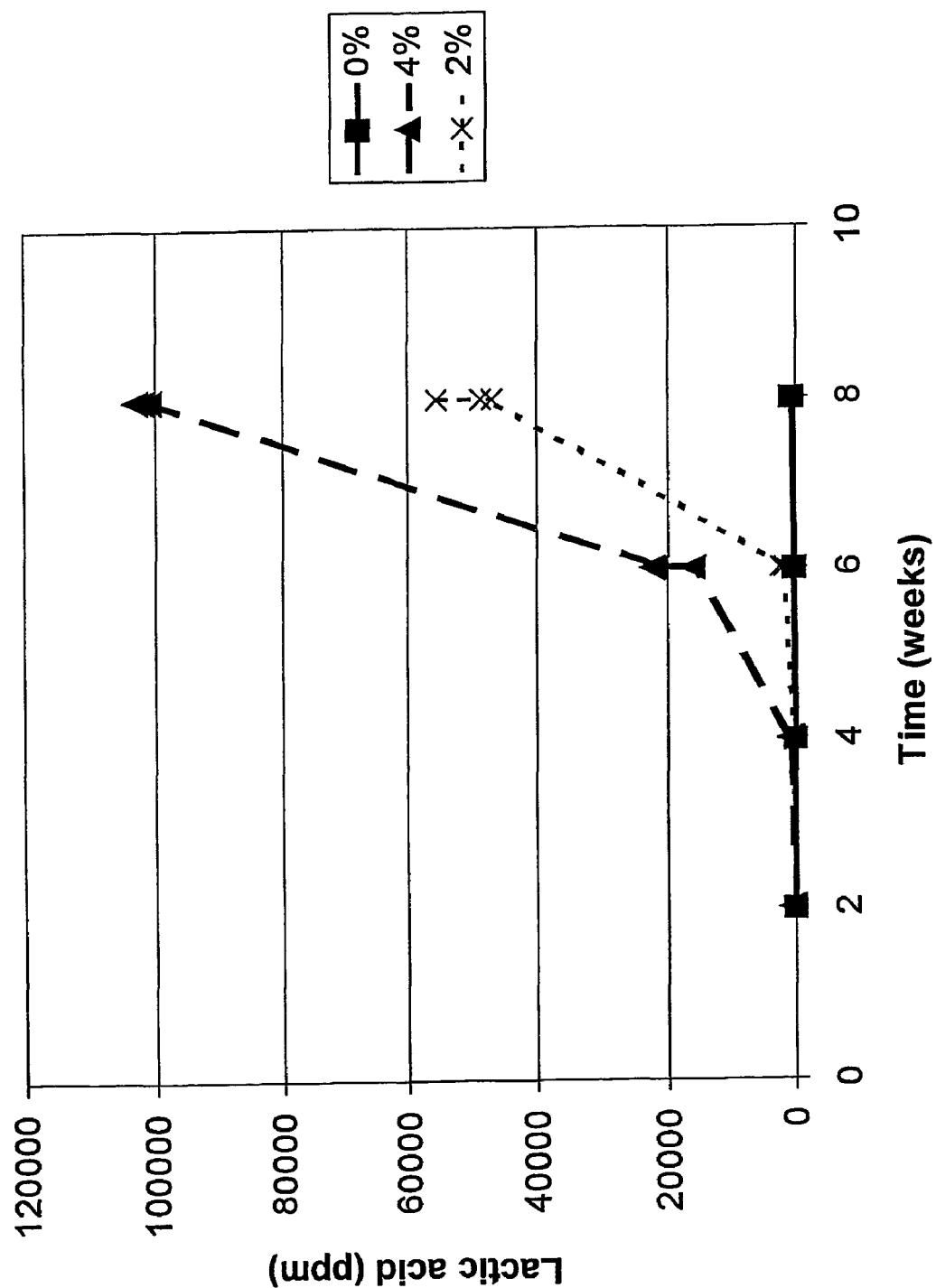

The decrease in molecular weight is reported in FIG. 4, the lactic acid released into the PBS buffer in FIG. 5.

EXAMPLE 3

A blend of poly(L-lactic acid) containing 5% lauric acid was prepared by first dry blending the solid materials and then solution blending the materials by roller mixing the solid mixture (10% by weight) with chloroform (90% by weight). After complete dissolution of the solids, the solutions were cast onto an open tray, left to dry (in a fume cupboard) at ambient temperature for 24 hours and dried for a further 24 hours under vacuum at ambient temperature. A control sample was also prepared by solution blending poly(L-lactic acid) alone with chloroform and drying the cast solution under the same conditions as the lauric acid-containing samples.

The dried cast films were then comminuted and extruded at 180° C. to produce rods with a diameter of approx 2 mm. The resultant rods were observed to be slightly opaque, but uniform in colour.

The rods were then subjected to simulated degradation by immersion in standard phosphate buffer solution (PBS), maintained at 37° C. for 8 weeks.

During the eight week test period samples of the billets were analysed:
- to determine molecular weight of the polymer blend (to measure the degree of degradation),
- to determine the tensile strength of the rods.

Figure 6:
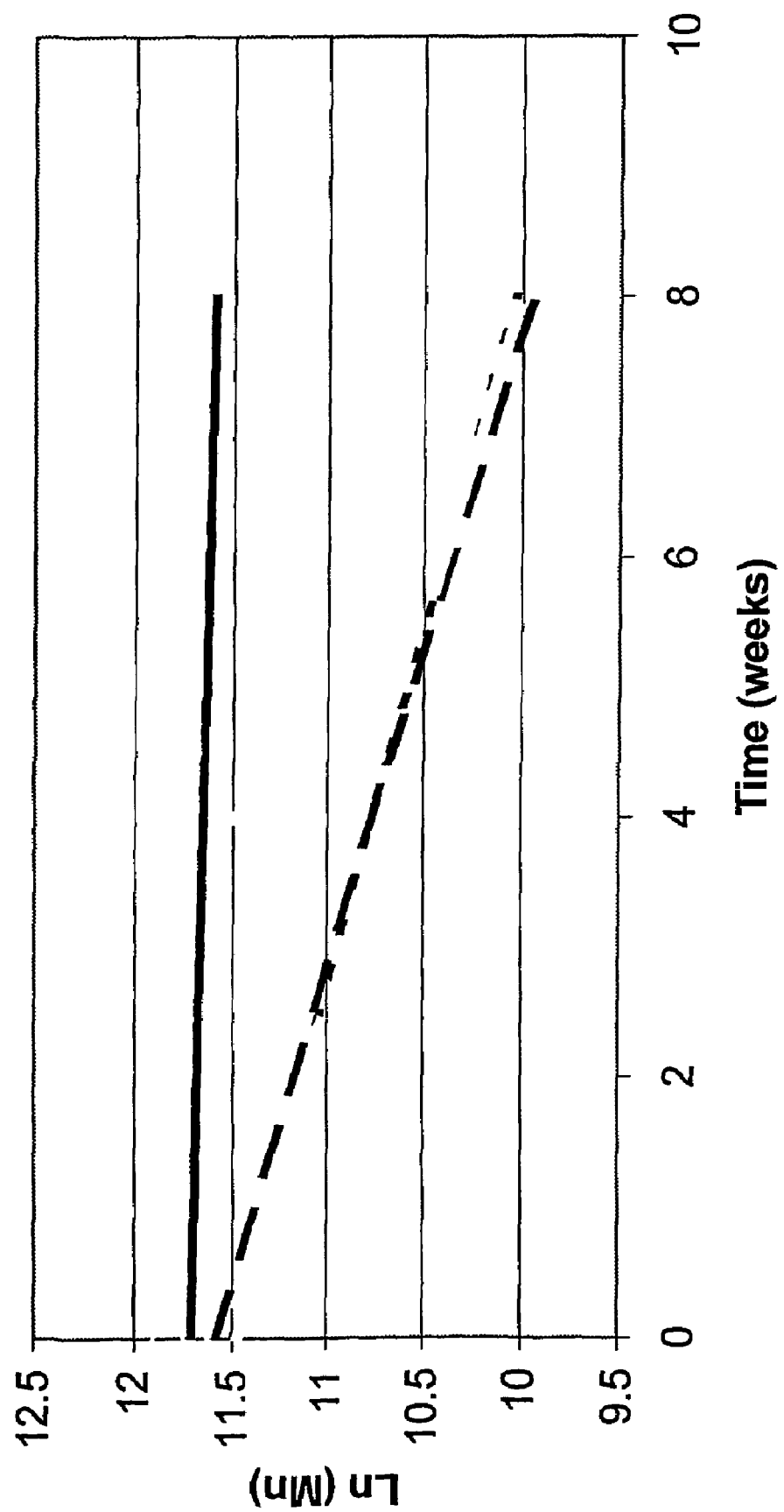
Figure 7:
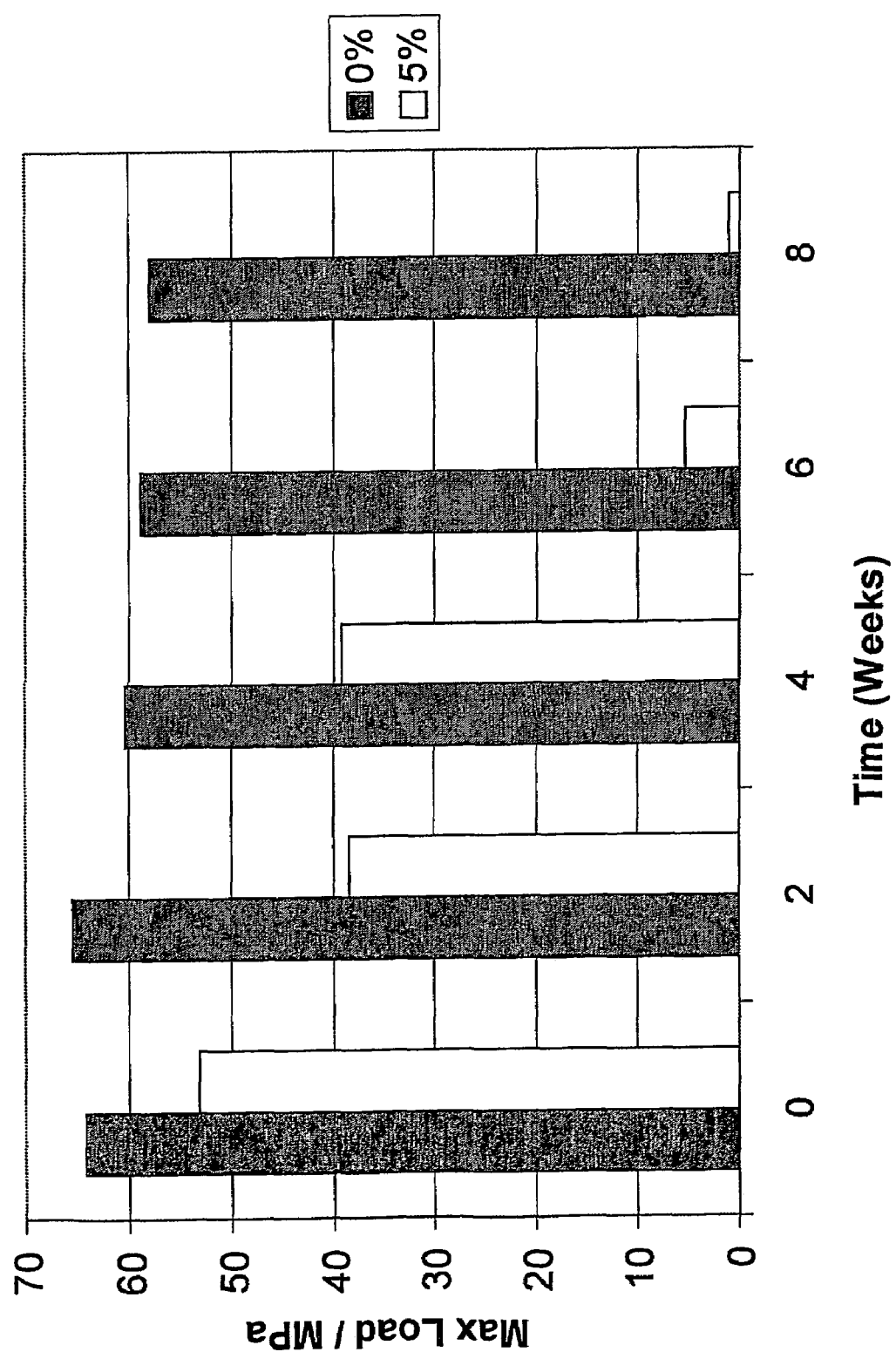

The decrease in molecular weight is reported in FIG. 6. The tensile strength of the rods was measured using a gauge length of 40 mm and a test speed of 10 mm/min, the results are reported in FIG. 7.

EXAMPLE 4

A blend of poly(L-lactic acid) containing 1% lauric acid was prepared by first dry blending the solid materials and then extruding the mixture at 195° C. The subsequent polymer blend was then analysed to determine the lauric acid content, which was measured at 0.9%. The resultant rod material was observed to be transparent.

EXAMPLE 5

Blends of poly(L-lactic acid) containing lauric anhydride, in amounts respectively, 2% and 5% by weight of the blend, were prepared by first dry blending the solid materials and then solution blending the materials by roller mixing the solid mixture (10% by weight) with chloroform (90% by weight). After complete dissolution of the solids, the solutions were cast onto an open tray, left to dry (in a fume cupboard) at ambient temperature for 24 hours and dried for a further 24 hours under vacuum at ambient temperature. A control sample was also prepared by solution blending poly(L-lactic acid) alone with chloroform and drying the cast solution under the same conditions as the lauric acid-containing samples.

The dried cast films were then comminuted and approximately 10 gm charges of the blends were compression moulded between two sheets of mould release sheets maintained 0.5 mm apart. The charges were warmed for 5 minutes prior to moulding and fed into the mould at a temperature of 195° C., pressure of 100N over a period of 90 seconds to form sheets. The resultant sheets were observed to be transparent.

The sheets were cut into strips and subjected to simulated degradation by immersion in standard phosphate buffer solution (PBS), maintained at 37° C. for 8 weeks.

Figure 8:
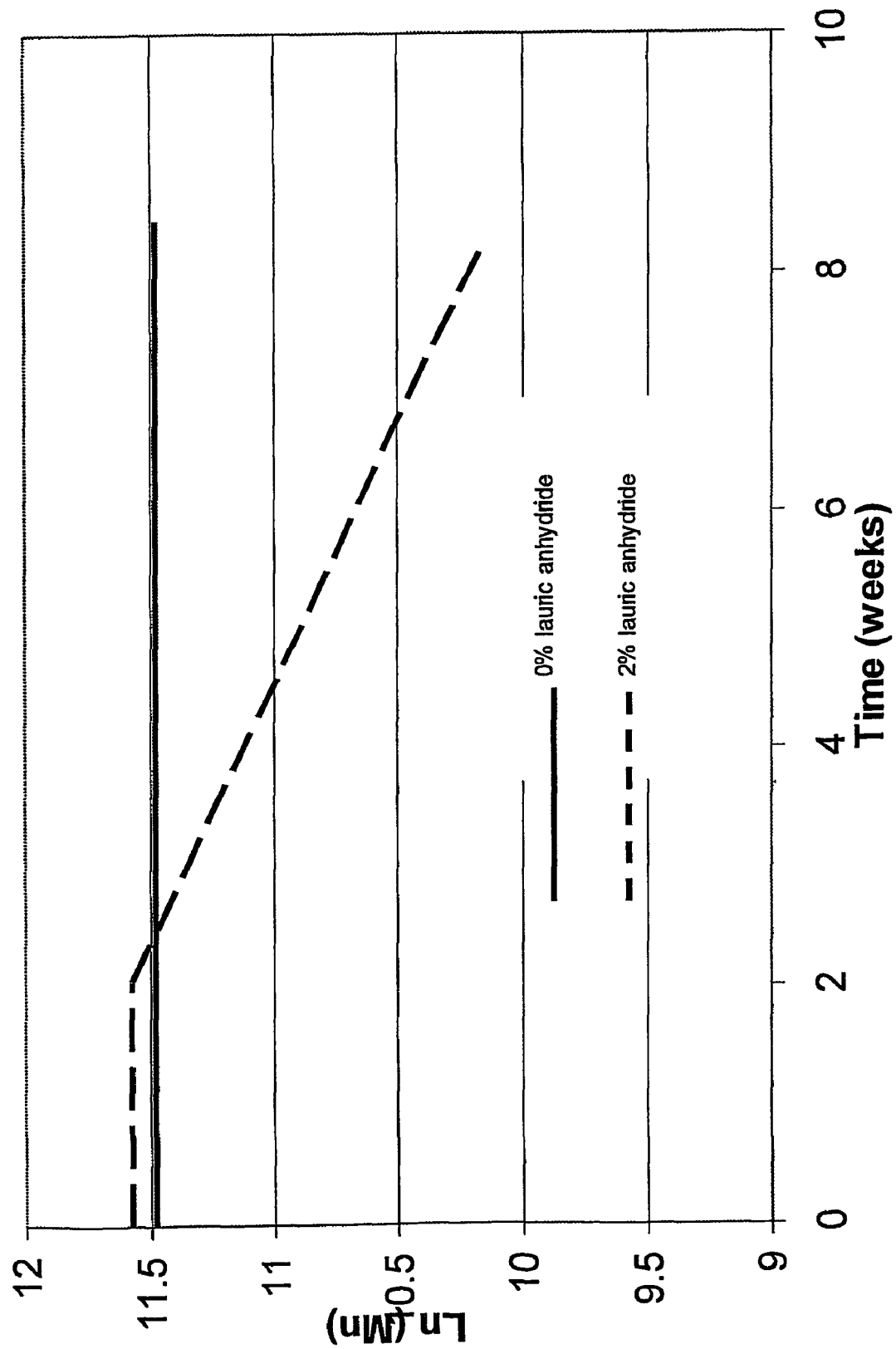

During the eight week test period samples of the sheets were analysed to determine molecular weight of the polymer blend (to measure the degree of degradation). The decrease in molecular weight is reported in FIG. 8.

EXAMPLE 6

Figure 9:
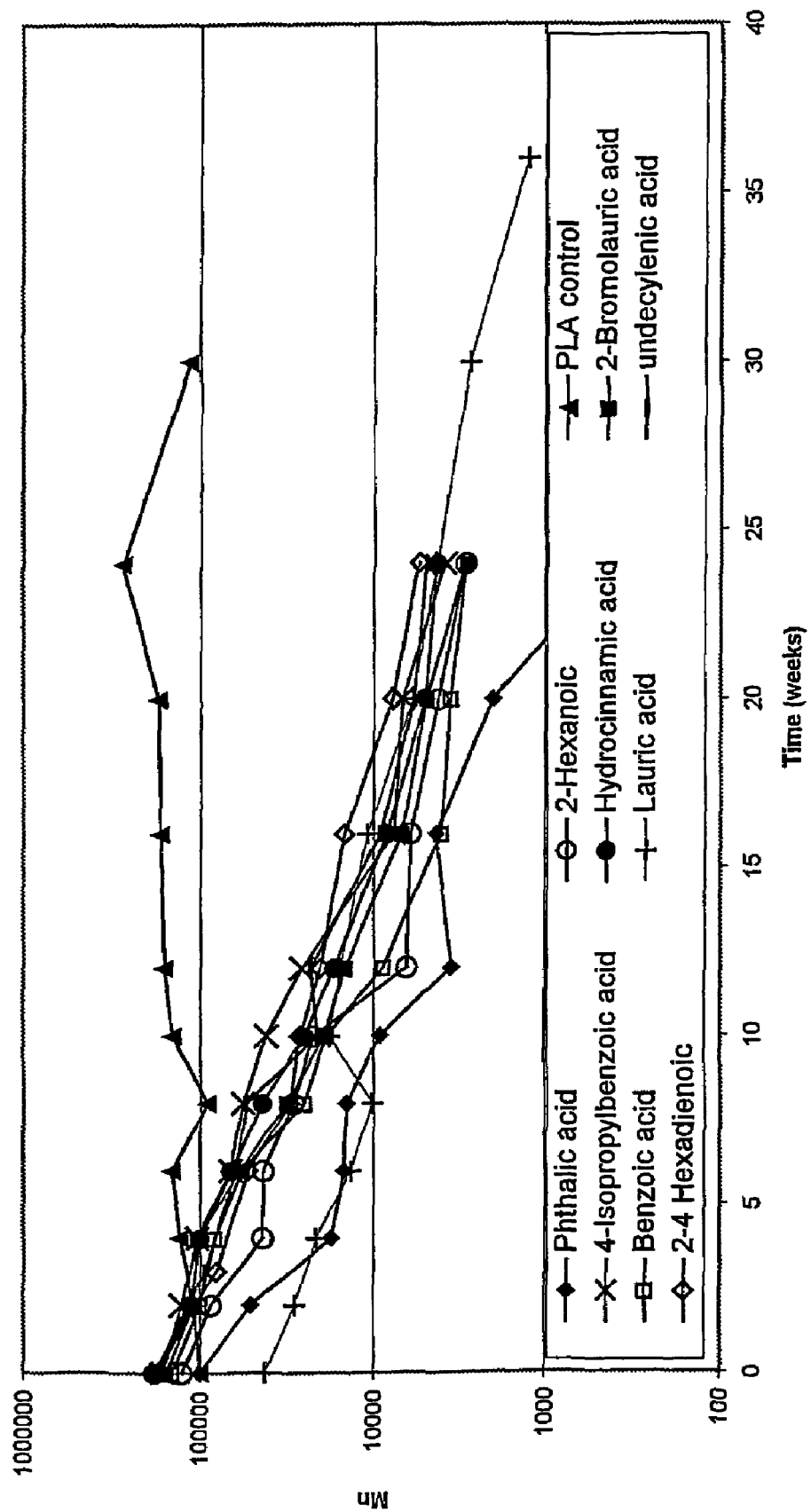

The process of Example 5 was repeated using a blend of poly (L-lactic acid) containing 2% by weight benzoic acid anhydride. The reduction of molecular weight with time is shown in FIG. 9.

The decrease in molecular weight over the twenty week test period showed that there was very little degradation (loss in molecular weight) within the first ten weeks

EXAMPLE 7

Figure 10:
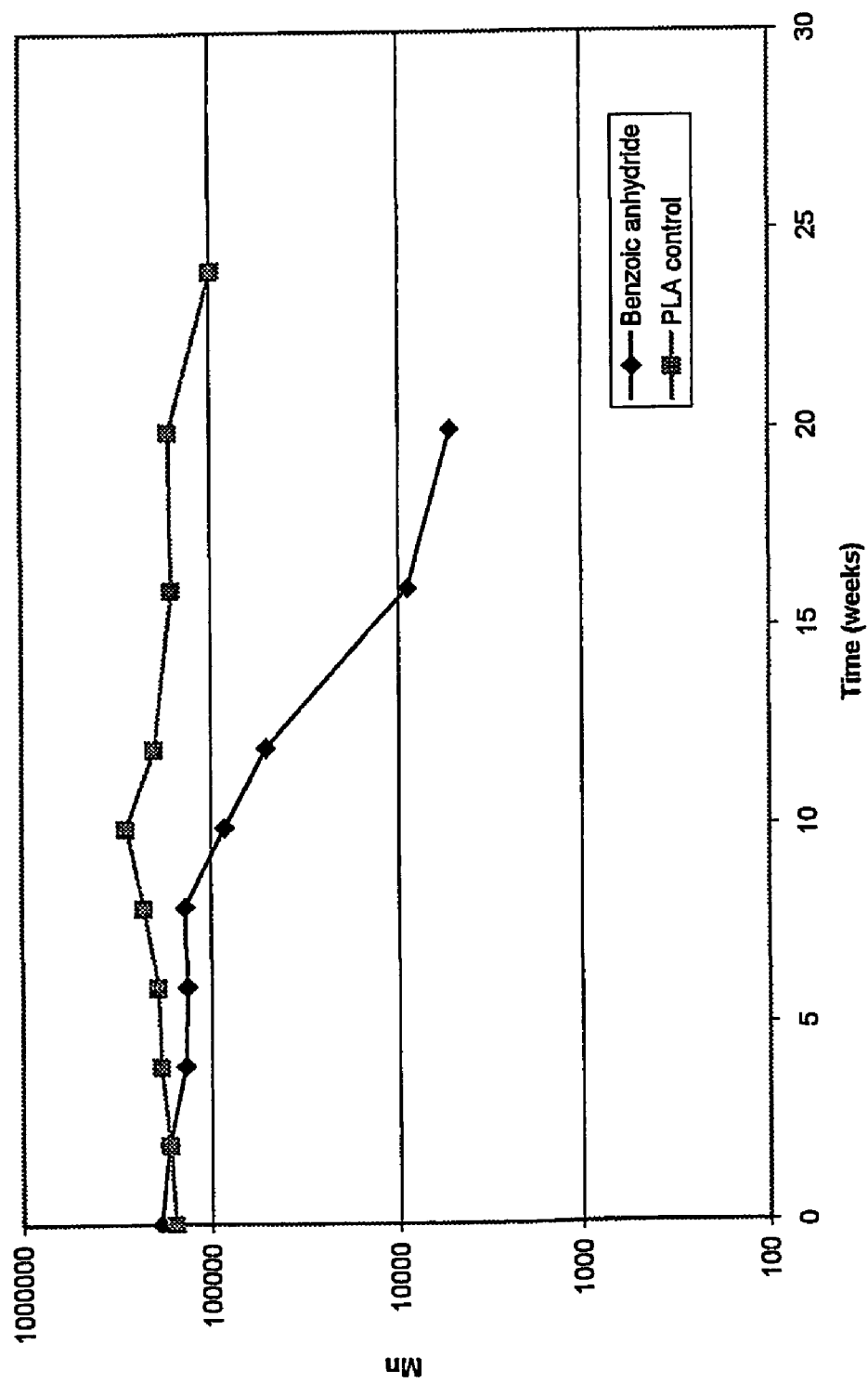

The process of Example 1 was repeated to make blends of poly (L-lactic acid) containing 2% by weight of the following acids:
Phthalic acid
2-Hexanoic
4-Isopropylbenzoic acid
Hydrocinnamic acid
2-Bromolauric acid
Benzoic acid
Lauric acid
Undecylenic acid
2-4 Hexadienoic
PLA control The results of a plot of molecular weight decreas with time is shown in FIG. 10.

EXAMPLE 8

The product of Example 4, ie rods of a blend of poly (L-lactic acid) containing 0.9% by weight of Lauric acid, were cut up into short lengths (typically about 3 mm). This material was then formed into an interference screw (for soft tissue anchorage) by injection moulding using an Arburg 270M All Rounder 500-90 machine with the following conditions:
Temp at nozzle=224° C.
Barrel Temp=235° C.
Injection pressure=1500 bar
Mould temp=18° C.

The resultant moulded devices had filled the mould well and were transparent.

The invention claimed is:

1. An implantable, biodegradable medical device formed from a homogeneous polymer blend comprising a lactic acid polymer in admixture, in an amount of not more than 10% by weight of the polymer blend, with an additive selected from the group consisting of isovaleric anhydride, hexanoic anhydride, decanoic anhydride, lauric anhydride, myristic anhydride, 4-pentenoic anhydride, oleic anhydride, linoleic anhydride, benzoic anhydride, poly(azelaic anhydride), 2-octen-1-ylsuccinic anhydride and phthalic anhydride.

2. The implantable, biodegradable medical device of claim 1, wherein the additive is selected from the group consisting of lauric anhydride and benzoic anhydride.

3. The implantable, biodegradable medical device of claim 1, wherein the polymer blend contains not more than 2% by weight of the additive.

4. The implantable, biodegradable medical device of claim 1, wherein the lactic acid polymer is poly lactic acid.

5. The implantable, biodegradable medical device of claim 1, wherein the lactic acid polymer is a copolymer with glycolic acid.

6. The implantable, biodegradable medical device of claim 1, wherein the polymer blend comprises additional polymeric compounds.

7. The implantable, biodegradable medical device of claim 1, wherein the polymer blend is a matrix component of a composite material from which the device is formed.

8. The implantable. biodegradable medical device of claim 1, in a form of a suture, suture anchor, soft tissue anchor, interference screw, tissue engineering scaffold, maxial-facial plate, or a fracture fixation plate or rod.

9. A polymer blend for manufacture of biodegradable medical devices, comprising polylactic acid in admixture with an additive in an amount of not more than 10% by weight of the polymer blend, the additive selected from the group consisting of isovaleric anhydride, hexanoic anhydride, decanoic anhydride, lauric anhydride, myristic anhydride, 4-pentenoic anhydride, oleic anhydride, linoleic anhydride, benzoic anhydride, poly(azelaic anhydride), 2-octen-1-yl-succinic anhydride and phthalic anhydride.

10. The polymer blend in of claim 9, comprising not more than 5% by weight of the additive.

11. The polymer blend in of claim 10, comprising no more than 2% by weight of the additive.

12. The polymer blend of claim 10, wherein the additive is selected from the group consisting of lauric anhydride and benzoic anhydride.

13. A polymer blend for the manufacture of biodegradable medical devices comprising a lactic acid polymer or a lactic acid copolymer in admixture, in an amount of not more than 10% by weight of the polymer blend, with an additive selected from the group consisting of lauric anhydride and benzoic anhydride.

14. An implantable, biodegradable medical device formed from a homogenous polymer blend comprising a lactic acid polymer in admixture, in an amount of not more than 10% by weight of the polymer blend, with an additive selected from the group consisting of lauric anhydride and benzoic anhydride.

* * * * *

UNITED STATES PATENT AND TRADEMARK OFFICE
CERTIFICATE OF CORRECTION

PATENT NO. : 7,524,891 B2  Page 1 of 1
APPLICATION NO. : 10/482371
DATED : April 28, 2009
INVENTOR(S) : Rose et al.

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by 542 days Delete the phrase "by 542 days" and insert -- by 831 days --

Signed and Sealed this

Twenty-fourth Day of August, 2010

David J. Kappos
*Director of the United States Patent and Trademark Office*